(12) United States Patent
Min et al.

(10) Patent No.: US 10,912,865 B2
(45) Date of Patent: Feb. 9, 2021

(54) RAPID PROTOTYPING AND IN VITRO MODELING OF PATIENT-SPECIFIC CORONARY ARTERY BYPASS GRAFTS

(71) Applicant: CORNELL UNIVERSITY, Ithaca, NY (US)

(72) Inventors: James K. Min, Brooklyn, NY (US); Bobak Mosadegh, New York, NY (US); Simon Dunham, New York, NY (US); Kranthi Kumar Kolli, New York, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 43 days.

(21) Appl. No.: 16/319,242

(22) PCT Filed: Jul. 22, 2017

(86) PCT No.: PCT/US2017/043425
§ 371 (c)(1),
(2) Date: Jan. 18, 2019

(87) PCT Pub. No.: WO2018/018033
PCT Pub. Date: Jan. 25, 2018

(65) Prior Publication Data
US 2019/0240377 A1    Aug. 8, 2019

Related U.S. Application Data

(60) Provisional application No. 62/365,474, filed on Jul. 22, 2016.

(51) Int. Cl.
*A61L 27/50* (2006.01)
*A61L 27/16* (2006.01)
(Continued)

(52) U.S. Cl.
CPC ............ *A61L 27/507* (2013.01); *A61B 6/032* (2013.01); *A61B 6/504* (2013.01); *A61L 27/16* (2013.01);
(Continued)

(58) Field of Classification Search
CPC ........ A61L 27/00; A61L 27/507; A61L 27/14; A61L 27/16; A61L 27/18; A61L 27/38; G06T 7/0012
(Continued)

(56) References Cited

U.S. PATENT DOCUMENTS

2008/0009781 A1   1/2008   Anwar et al.
2016/0117816 A1   4/2016   Taylor
(Continued)

FOREIGN PATENT DOCUMENTS

WO    WO-00/41648        7/2000
WO    WO-2015/061907 A1  5/2015

OTHER PUBLICATIONS

International Search Report and Written Opinion, PCT/US2017/043425, Cornell University, 6 pages (dated Oct. 12, 2017).
(Continued)

*Primary Examiner* — John P Lacyk
(74) *Attorney, Agent, or Firm* — Foley & Lardner LLP

(57) ABSTRACT

The present disclosure describes a system and a method for producing patient-specific small diameter vascular grafts (SDVG) for coronary artery bypass graft (CABG) surgery. In some embodiments, the method for producing SDVGs includes non-invasive quantification of patient-specific coronary and vascular physiology by applying computational fluid dynamics (CFD), rapid prototyping, and in vitro techniques to medical images and coupling the quantified patient-specific coronary and vascular physiology from the
(Continued)

CFD to computational fluid-structure interactions and SDVG structural factors to design a patient-specific SDVG.

22 Claims, 11 Drawing Sheets

(51) Int. Cl.

| | |
|---|---|
| *A61L 27/18* | (2006.01) |
| *G06K 9/00* | (2006.01) |
| *A61L 27/38* | (2006.01) |
| *G06T 7/62* | (2017.01) |
| *A61B 6/03* | (2006.01) |
| *A61B 6/00* | (2006.01) |
| *G06T 7/00* | (2017.01) |

(52) U.S. Cl.
CPC ............... *A61L 27/18* (2013.01); *A61L 27/38* (2013.01); *G06K 9/00* (2013.01); *G06T 7/0012* (2013.01); *G06T 7/62* (2017.01); *G06K 2209/05* (2013.01); *G06T 2207/10072* (2013.01); *G06T 2207/30104* (2013.01)

(58) Field of Classification Search
USPC ............................................. 600/36
See application file for complete search history.

(56) References Cited

U.S. PATENT DOCUMENTS

| | | |
|---|---|---|
| 2016/0125161 A1 | 5/2016 | Sankaran et al. |
| 2016/0136326 A1 | 5/2016 | Fisher et al. |

OTHER PUBLICATIONS

Bolton et al., "Seroma Formation Associated with PTFE Vascular Grafts used as Arteriovenous Fistulae," Dialysis & Transplantation, John Wiley & Sons Inc., US, vol. 10, No. 1, Jan. 1, 1981, XP000913632, ISSN: 0090-2934, pp. 60-66.

Extended European Search Report in EP Patent Application No. 17832012.3 dated Jan. 16, 2020 (10 pages).

Shombert, David G. "Measurement of Turbulent Flow in Vascular Grafts" Proceedings of the Annual Northeast Bioengineering Conference. Boston, Mar. 27-28, 1989; [Proceedings of the Annual Northeast Bioengineering Conference], New York, IEEE, US vol. Conf. 15, Mar. 27, 1989, XP000041654, pp. 85-86.

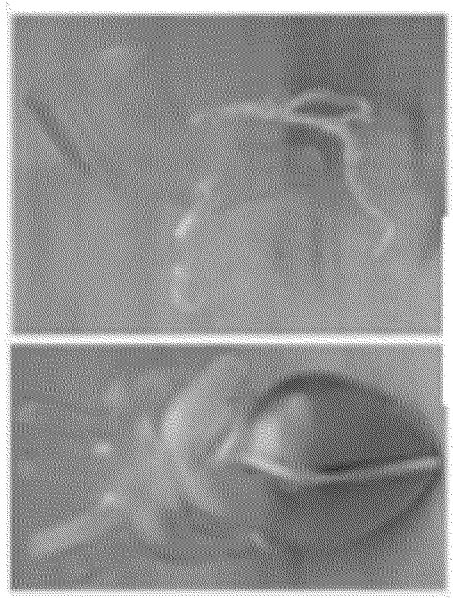
FIG. 5A
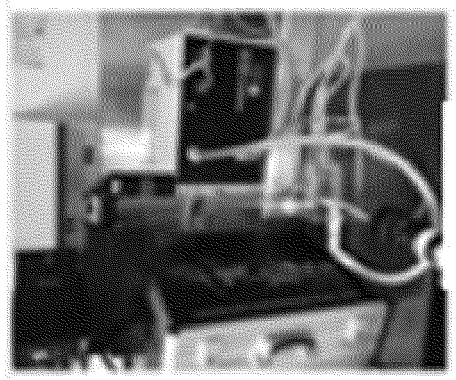
FIG. 5B
FIG. 5C
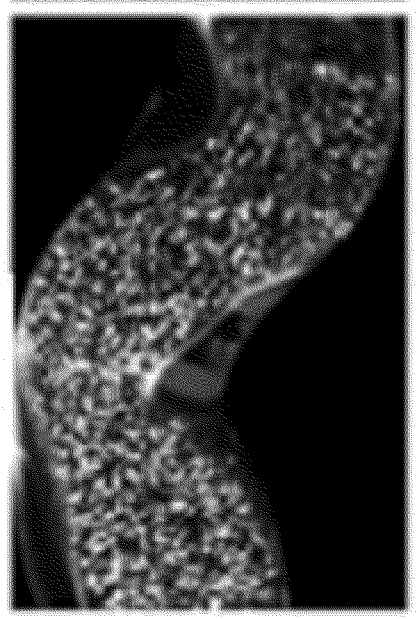
FIG. 5D
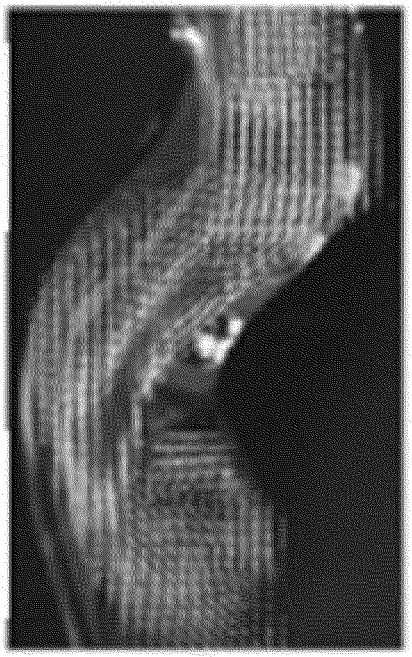

RAPID PROTOTYPING AND IN VITRO MODELING OF PATIENT-SPECIFIC CORONARY ARTERY BYPASS GRAFTS

CROSS-REFERENCE TO RELATED APPLICATIONS

This application is a National Stage Application of PCT/US2017/043425, filed Jul. 22, 2017, which claims the benefit of and priority to U.S. Provisional Patent Application No. 62/365,474, filed on Jul. 22, 2016 and titled COMPUTATIONAL MODELING AND RAPID PROTOTYPING OF PATIENT-SPECIFIC CORONARY ARTERY BYPASS GRAFTS, which is hereby incorporated by reference in its entirety.

BACKGROUND

The following description is provided to assist the understanding of the reader. None of the information provided or references cited is admitted to be prior art to the present technology.

Coronary artery disease (CAD) is a large cause of patient morbidity and mortality. In the United States, CAD affects more than 16 million adults, accounts for more than ⅓ of deaths, and is responsible for more than 1.2 million hospitalizations annually. Despite medical therapy, coronary revascularization is required for more than 1.5 million individuals annually. For stable individuals with complex multivessel disease, a coronary artery bypass graft (CABG) remains the mainstay of treatment for myocardial ischemia reduction and is performed for nearly 400,000 individuals in the U.S. annually.

Post-CABG morbidity and mortality remain high. Early CABG occlusion—particularly of saphenous venous grafts (SVG)—occurs in 10% of grafts, with 50% failing by 18 months. Further, 30% of individuals do not even possess the suitable autologous conditions for CABG. Autologous grafts can be produced in a variety of sizes. In general, small diameter grafts can include grafts having diameters of less than about 6 mm. Medium diameter grafts can include grafts having diameters between about 6 mm and about 8 mm. Large diameter grafts can include grafts having diameters of greater than about 8 mm.

Common to the failure of small diameter vascular grafts (SDVG) has been an array of overlapping factors, with inadequate consideration of the totality of variables that influence long-term SDVG patency. These can include: (i) patient-specific cardiothoracic anatomy and physiology to inform graft size, location, angle and path for optimized flow; (ii) SDVG features such as mechanical properties that ensure adequate graft compliance to accommodate pulsatile flow states while avoiding kinking and diminished durability, and surface biocompatibility to minimize inflammation and platelet adhesion; and (iii) surgical-related factors, such as optimal revascularization strategies to properly locate grafts to specific arteries to relieve ischemia, as well as to minimize anastomotic occlusion or flow reduction.

SUMMARY

According to one aspect of the disclosure, a method includes receiving at least one medical image of a subject. The method also includes determining a coronary artery volumetric geometry of the subject. The volumetric geometry is determined responsive to the at least one medical image. The method further includes generating a patient-specific vascular graph model responsive to the determined coronary artery volumetric geometry. The method further includes determining, using the patient-specific vascular graph model, a hemodynamic profile. The method further includes producing a patient-specific vascular graft based on the hemodynamic profile and the determined coronary artery volumetric geometry.

In some implementations, the method can include printing the patient-specific vascular graft with a 3D printer. The patient-specific vascular graft can have an internal diameter between about 0.5 mm and about 6 mm. In some implementations, the patient-specific vascular graft is formed from a biocompatible polymer. In some implementations, the patient-specific vascular graft exhibits continuously spatially varying mechanical properties along at least a portion of its length.

In some implementations, determining the coronary artery volumetric geometry can include determining an artery centerline of the coronary artery. The method can also include performing lumen segmentation of the coronary artery volumetric geometry. In some implementations, the method can include calculating at least one of a flow, a velocity, a pressure, or a shear stress of the patient-specific vascular graft.

In some implementations, calculating at least one of the flow, the velocity, the pressure, or the shear stress of the patient-specific vascular graft can include providing a flow system comprising a pump, the patient-specific vascular graft, and at least one measurement tool. The at least one measurement tool can be at least one of a pressure gauge, a flow gauge, a velocity gauge, a particle image velocimetry device, a pressure guide wire, a flow guide wire, an optical coherence tomography device, or a strain sensor. In some implementations, generating the hemodynamic profile can further include applying an optimization technique based on a set of parameters including at least one of a flow rate, a pressure gradient, a shear stress, or a flow oscillation. In some implementations, the at least one medical image includes at least one computed tomographic angiography (CTA) image.

According to another aspect of the disclosure, a system includes at least one processor and a memory unit that stores processor executable instructions. When the at least one processor executes the processor executable instructions, the at least one processor receives at least one medical image of a subject. The processor also determines a coronary artery volumetric geometry of the subject responsive to the at least one medical image. The processor generates a patient-specific vascular graph model responsive to the determined coronary artery volumetric geometry. The processor also determines, using the patient-specific vascular graph model, a hemodynamic profile. The processor also generates instructions for producing a patient-specific vascular graft based on the hemodynamic profile and the determined coronary artery volumetric geometry.

In some implementations, execution of the processor executable instructions causes the at least one processor to transmit the instructions to a 3D printer. In some implementations, the instructions for producing the patient-specific vascular graft indicate that the patient-specific vascular graft should be formed from a biocompatible polymer. In some implementations, the instructions for producing the patient-specific vascular graft indicate that the patient-specific vascular graft should exhibit continuously spatially varying mechanical properties along at least a portion of its length.

In some implementations, execution of the processor executable instructions further causes the at least one processor to determine the coronary artery volumetric geometry by determining an artery centerline of the subject. In some implementations, execution of the processor executable instructions further causes the at least one processor to perform a lumen segmentation of the coronary artery volumetric geometry.

In some implementations, execution of the processor executable instructions further causes the at least one processor to calculate at least one of a flow, a velocity, a pressure, or a shear stress of the patient-specific vascular graft.

In some implementations, execution of the processor executable instructions further causes the processor to calculate at least one of the flow, the velocity, the pressure, or the shear stress of the patient-specific vascular graft based on an output received from at least one measurement tool included within a flow system including a pump and the patient-specific vascular graft. In some implementations, the at least one measurement tool includes at least one of a pressure gauge, a flow gauge, a velocity gauge, a particle image velocimetry device, a pressure guide wire, a flow guide wire, an optical coherence tomography device, or a strain sensor. In some implementations, the at least one medical image includes at least one (CTA) image.

BRIEF DESCRIPTION OF DRAWINGS

The figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 5A illustrates a patient-specific vascular graft as a 3D printed physical model.

FIG. 5B illustrates an example in vitro flow circulation system.

FIGS. 5C and 5D illustrate the tracking of particle movements and computing of pulsatile fluid velocities within small-diameter tubular models.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

In general, the present disclosure describes a system and a method for producing and validating patient-specific small diameter vascular grafts (SDVG), and models thereof, for coronary artery bypass graft (CABG) surgery. The system can generate patient-specific mathematical and physical models of SDVGs that reflect realistic physiologic conditions, which can enable individual and integrated assessment of features that encourage graft patency, and subsequent use of the optimized model for in vivo implantation. In some implementations, the SDVG has an internal diameter between about 0.5 mm and about 6 mm. In some embodiments, the method for producing SDVGs includes non-invasive quantification of patient-specific coronary and vascular physiology by applying computational fluid dynamics (CFD) to one or more medical images and coupling the quantified patient-specific coronary and vascular physiology from the CFD to computational fluid-structure interactions and SDVG structural factors to design a patient-specific SDVG. In some implementations, the medical images can be generated using magnetic resonance imaging (MRI), magnetic resonance angiography (MRA), or computed tomographic angiography (CTA).

Figure 1:
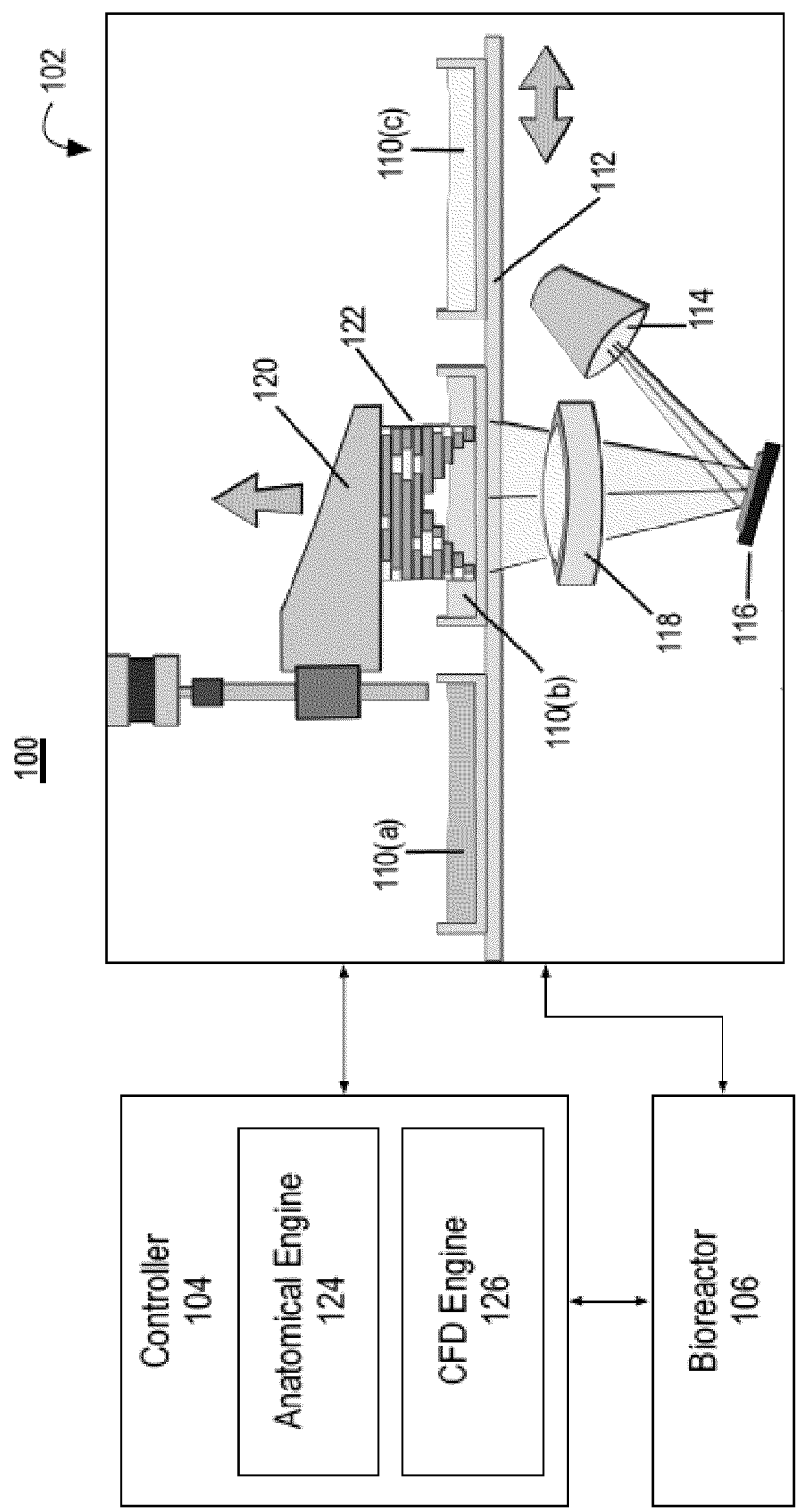
FIG. 1 illustrates an example system for producing a patient-specific vascular graft.
Figure 2:
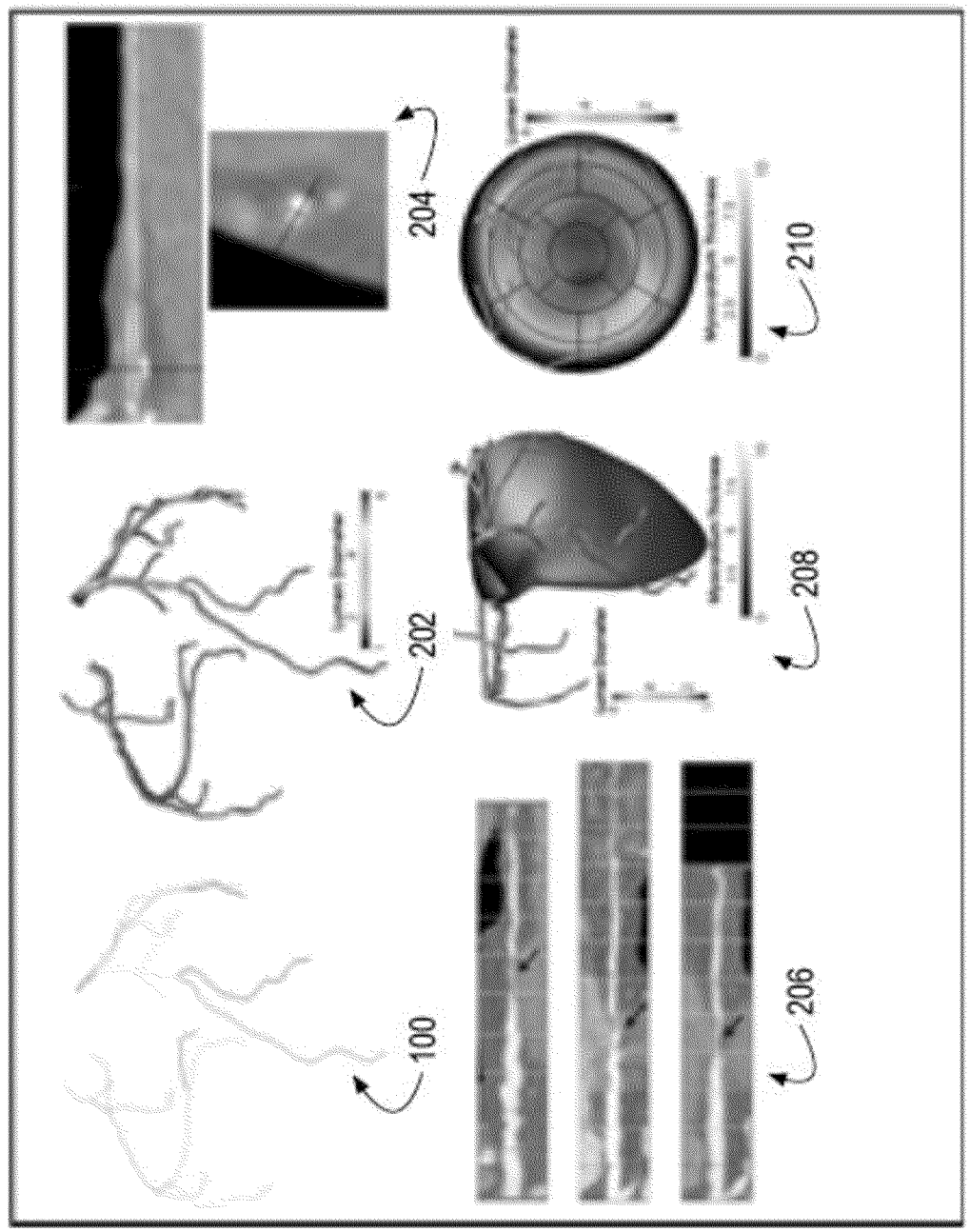
FIG. 2 illustrates a 3D image-based modeling of coronary arteries and myocardium.

FIG. 1 illustrates a system 100 for designing and generating a patient-specific SDVG. The system 100 includes a printing subsystem 102, a controller 104, and a bioreactor 106. The printing subsystem 102 includes a plurality of vats 110(a)-110(c) (collectively referred to as vats 110). The vats 110 are positioned atop a translating stage 112. A light source 114, mirror 116, and lens 118 are positioned below the translating stage 112. The printing subsystem 102 also includes a build platform 120. A patient-specific SDVG 122 is coupled to the build platform 120. The controller 104 includes an anatomical engine 124 and a CFD engine 126.

The system includes a printing subsystem 102 that is configured to manufacture the patient-specific SDVG 122 after the patient-specific SDVG 122 is designed by the controller 104. In some implementations, the printing subsystem 102 can be any 3D printing system. In other implementations, the printing subsystem 102 can be a multi-material bioprinting stereolithography system that can fabricate complex composite cellular seeded hydrogels. As an overview, the printing subsystem 102 can include a plurality of vats that each includes different bioinks. The bioinks can include different resin compositions. The compositions can include different concentrations and species of monomer, crosslinkers, cells, and other ingredients. The different bioinks can be used to form different layers of the printed biomaterial. As described below, the bioprinter can enable high resolution control of the printed biomaterial. The high resolution of the bioprinter enables the development of a local cellular environment that both chemically and physically provides the correct stimuli for proliferation, differentiation, and migration of seeded cells. In some implementations, multiple cell types can be seeded in adjacent layers. The system described herein enables the fabrication of complex hierarchies of different hydrogels that provide an accurate synthetic facsimile of intricate biological tissues.

The printing subsystem 102 can solidify distinct bioinks into 3D structures using visible light at a resolution of about 30 μm. The printing subsystem 102 can build the tissue in a layer-by-layer fashion, in which each layer can include three (or more) distinct custom-made bioinks, with patterned voids that can form the lumen of the patient-specific SDVG 122.

The printing subsystem 102 includes the translating stage 112. The translating stage 112 is configured to translate across a horizontal plane. In some implementations, the translating stage 112 can translate in a single direction along the horizontal plane, and, in other implementations, the translating stage 112 can translate along multiple directions of the horizontal plane. The translating stage 112 is optically transparent to the light generated by the light source 114 such that light can pass through the translating stage 112 to the vats 110.

The printing subsystem 102 also includes vats 110 that are coupled to a top surface of the translating stage 112. Each of the vats 110 hold a different fluid used in the bioprinting process. For example, the fluids can include bioinks and cleaning solutions. The controller 104 is configured to position a different one of the vats 110 under the build platform 120. The bottom of the vats 110 are optical transparent to the light generated by the light source 114 such that light passing from the light source 114 (and through the translating stage 112) can pass to the liquid held in the vat 110. In some implementations, the interior, bottom surface of each of the vats 110 is coated with a Teflon coating to prevent cured bioink layers from sticking to the vat 110. In some implementations, the cleaning solution includes a solvent bath that can contain, for example, isopropyl alcohol. In some implementations, the system can also include a mechanical cleaning, such as a rubber wiper, that removes excess bioink.

The bioinks stored in the vats 110 are cured (or otherwise solidified) by light emitted by the light source 114. In some implementations, the printing subsystem 102 can include between about 1 and about 10, between about 1 and about 5, or between 1 and about 3 vats 110 that each store different types of bioinks. The bioinks can include a photo-curable hydrogel and the primary cell type of the intima (e.g., endothelial cells), media (e.g., smooth-muscle cells), or adventitia (e.g., fibroblast). In some implementations, the bioinks can include biocompatible hydrogels that polymerize in visible light. The bioinks can include a hydrogel recipe that includes photoinitiators, co-initiators, and radical scavengers that prevent undesired polymerization beyond the mask.

The printing subsystem 102 also includes a light source 114. Layers of the bioinks are iteratively cured by light emitted from the light source 114. In some implementations, the light source 114 generates light in the visible spectrum and in other implementations the light source 114 generates ultraviolet light. In some implementations, the light source 114 includes a laser or an array of LEDs with galvanometers.

The light source 114 of the printing subsystem 102 projects light (in the visible or ultraviolet range) onto the mirror 116. In some implementations, the mirror 116 includes an array of digital mirror devices (DMD). Each of the DMDs can form a "pixel" of a mask. In these implementations, the controller 104 controls the state of each of the DMDs to generate the mask. When a DMD is on, it reflects light form the light source 114 toward the build platform 120. When a DMD is off, it does not reflect light. The controller 104 configures the DMDs such that the mask corresponds to the next layer of the bioprinted part 122. The use of DMDs enables an entire layer of the bioprinted part 122 to be cured at once. In other implementations that do not use DMDs, the generated light source (e.g., laser beam) is rastered across the bottom of the vat 110 to cure the bioink. In some implementations, the use of DMDs makes the printing subsystem 102 less sensitive to alignment issues experienced by nozzle-based extrusion printers. The printing subsystem 102 also includes a lens 118 that can focus the projected light onto the bottom of the translating stage 112 underneath the build platform 120.

In some implementations, the system 100 can include a bioreactor 106 that can include a pulsatile flow pump, tubing, acrylic case, pressure sensors, and flow meters. The bioreactor 106 can recirculate media through the patient-specific SDVG 122. Using pressure sensors, the pulsatile flow can be tracked.

In some implementations, applying physiological pulsatile flow can promote proper alignment and maturation of the cells and extra-cellular matrix (ECM) in the artery. The artery can be conditioned for various time points (e.g., weekly for up to two months) and evaluated for its cellular viability and burst pressure.

In some implementations, the bioprinted artery can be responsive to flow via vasoconstriction/dilation. Using the bioreactor, various steady-state flow rates can be applied while images are continuously captured by a camera. The response to various frequency and amplitudes of pulsatile flow will be measured to characterize the dynamics of the smooth muscle cells.

The system 100 also includes the controller 104. In some implementations, the controller 104 can be implemented with a general purpose processor, microcontroller, a field-programmable gate array (FPGA), or an application specific integrated circuit (ASIC). In some implementations, the controller 104 can control the positioning of the vats 110 in relation to the build platform 120. The controller 104 can also control the intensity and duration of the light emitted from the light source 114. The controller 104 can also control the generation of a mask with the mirror 116.

The controller 104 includes the anatomical engine 124 and the CFD engine 126. In some embodiments, the CFD engine 126 and the anatomical engine 124 can determine factors for the patient-specific SDVG 122 such as, but not limited to, flow, velocity, pressure, energy loss, shear stress, and force that the patient-specific SDVG 122 should withstand. The controller 104 can also generate the 3D structure of patient-specific SDVG 122. In some embodiments, when printed, the patient-specific SDVG 122 can substantially replicate in vitro graft hemodynamics and wall mechanics and other factors as determined by the CFD engine 126 and anatomical engine 124. In some embodiments, the printed patient-specific SDVG 122 can maintain sufficient blood flow, reduce thrombosis, and reduce inflammation after implantation.

By way of example, but not by way of limitation, consider two patients being considered for CABG with marked clinical heterogeneity. As seen in Table 1, patient-specific differences may appreciably affect SDVG patency for a multitude of reasons, including graft size, location, angle and path, microcirculatory resistance, flow and perfusion pressure, and revascularization strategy. Other factors such as competitive and collateral flow are also vital.

TABLE 1

Patient-Specific Clinical Characteristics

| | Age | Hypertension | Diabetes | BMI | Coronary tortuosity | Aortic tortuosity |
|---|---|---|---|---|---|---|
| Anatomic and Physiologic Factors Influencing CABG Patency | 75<br>60<br>Microcirculatory resistance | Hypertensive<br>Normotensive<br>Microcirculatory resistance | Diabetic<br>Non-diabetic<br>Microcirculatory resistance<br>Perfusion pressure | 32<br>24<br>Graft size | Tortuous<br>Non-tortuous<br>Graft location/ angle/ path | Tortuous<br>Non-tortuous<br>Graft location/ angle/ path |

Patient-Specific Clinical Characteristics

| | Known MI | CAD extent and severity | Ischemia/ Fibrosis | Ejection Fraction |
|---|---|---|---|---|
| | Prior MI | LAD, LCx | +/+ | 15% |
| | No prior MI | LAD, PDA, PL | +/− | 75% |
| Anatomic and Physiologic Factors Influencing CABG Patency | Microcirculatory resistance | Revascularization strategy, flow | Flow/ perfusion pressure | Flow/ perfusion pressure |

BMI = body mass index;
MI = myocardial infarction;
CAD = coronary artery disease;
LAD = left anterior descending artery;
LCx = left circumflex artery;
PDA = posterior descending artery;
PL = posterolateral branch artery In some embodiments, patient-specific hemodynamics are integrated into the production of patient-specific SDVGs by the CFD engine 126. By way of example, but not by way of limitation, in some embodiments, patient-specific hemodynamics include, but are not limited to, oscillation, stagnation, energy loss of flow through the graft, wall mechanics (e.g., low shear stress and lateral traction on the graft wall), and graft-artery compliance mismatch.

EXAMPLES

The present technology is further illustrated by the following examples, which should not be construed as limiting in any way.

Example 1

CTA of the coronary arteries can be a non-invasive option to the invasive coronary angiography (ICA). In some implementations, the anatomical engine 124 is configured to receive motion-free images (e.g., CTA images) at isotropic spatial resolution of about 500 μm. In one example, the system 100 performed CTA on 230 patients prior to ICA irrespective of body mass index or heart rate. For stenosis severity, CTA demonstrated a sensitivity, specificity, positive predictive value, and negative predictive value of 94%, 83%, 48%, and 99%, respectively, compared to ICA.

The anatomical engine 124 can receive the CTA data to generate 3D coronary artery geometries for image-based modeling of the coronary anatomy. The anatomical engine 124 determines the artery centerline extraction 200. Using the center line extraction, the lumen segmentation and stenosis 202 can be performed. The anatomical engine 124 can also perform vessel wall segmentation and plaque detection 204 and artery co-registration 206. The anatomical engine 124 can also perform myocardial segmentation with 3D artery overlay 208. The anatomical engine 124 can also generate a 17-segment model with 2D flattened artery overlay 210.

Example 2

Figure 3:
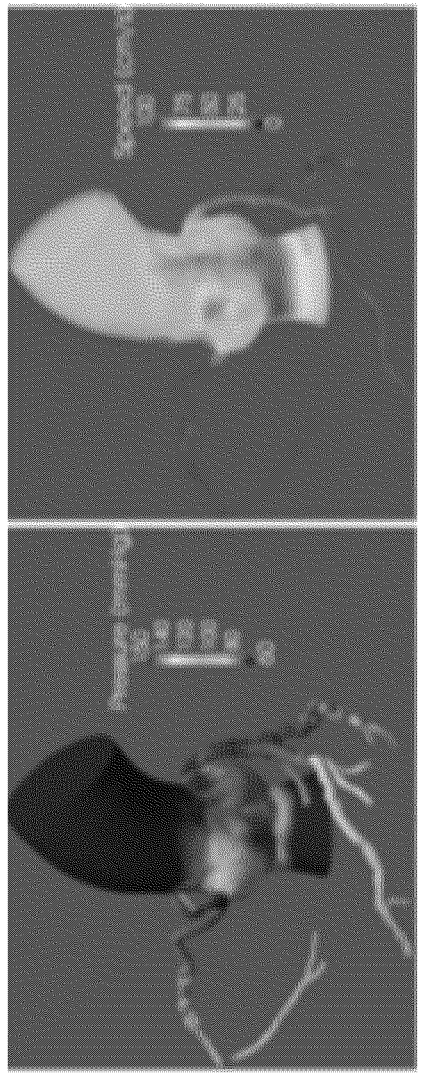
FIG. 3 illustrates an example calculation of coronary pressure and velocity.
Figure 4:
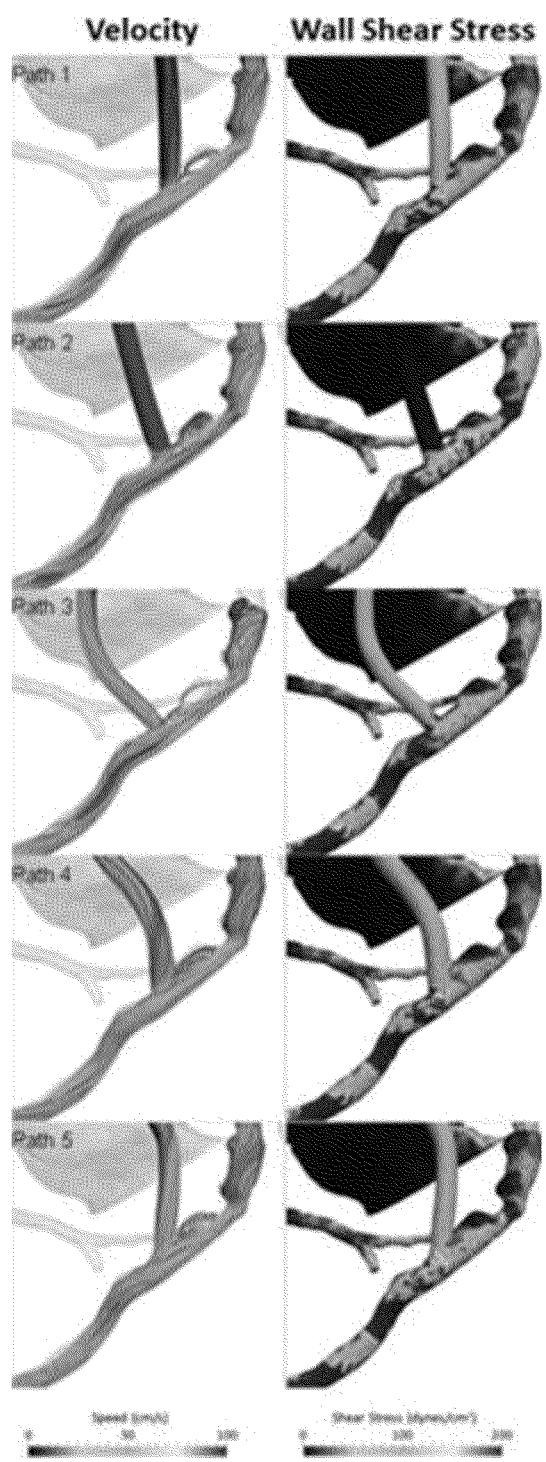
FIG. 4 illustrates the differences in velocities (left) and wall shear stress (right) with respect to angle of anastomoses.

In some implementations, the anatomical engine 124 can generate anatomic information about the patient-specific SDVG. The CFD engine 126 can generate a hemodynamic profile by performing computational fluid dynamics on the anatomic information. In general, the hemodynamic profile can include clinical factors, design factors, or other factors, such as flow oscillation, flow stagnation, flow energy loss, wall mechanics, shear levels, and graft-artery compliance mismatch. The CFD engine 126 can calculate the hemodynamic (e.g., physiologic) data of the aortic and coronary artery flow and pressure. FIG. 3 illustrates the pressure, velocity, and flow, as calculated by the CFD engine 126, in a patient-specific SDVG 122. In some implementations, the CFD engine 126 can plan "virtual" revascularization strategies by selection of coronary vessels and locations within vessels to be revascularized for flow features and ischemia reduction. FIG. 4 illustrates a patient-specific SDVG 122 after percutaneous coronary revascularization.

In some implementations, to increase the throughput of patient-specific analysis, the system can automate parameterized model generation. Using a patient-specific geometry, a range of perturbed mathematical models and simulation meshes are generated according to design parameters of interest. Modeling, meshing, submission and retrieval of simulation data for CFD are automatically run by a script, enabling batch testing of all CABG configurations.

In some implementations, the in vitro flow model can be used to calculate the wall shear stress (WSS) of the patient-specific SDVG 122 (Table 2). WSS has been implicated in the pathogenesis of neo-intimal hyperplasia and thrombus formation.

TABLE 2

| | CABG Variables | In-silico | In-vitro | Design Objective |
|---|---|---|---|---|
| Hemodynamics | Flow rate | CFD | Flow wire; PIV | Maximize |
| | Pressure gradient | CFD | Pressure wire | Minimize |
| | Flow separation | CFD | PIV | Minimize |
| | Energy loss | CFD | Pressure wire; PIV | Minimize |
| | Particle residence time | CFD | PIV | Minimize |
| | Blood stress-strain rate behavior | CFD | Rheometer | Physiologic range |
| Wall Mechanics | Shear stress and traction | CFD | PIV | physiologic range |
| | Oscillatory shear index | CFD | PIV | Physiologic range |
| | Deformation and strain | FSI | PIV High-speed camera Strain sensors | Physiologic range |
| | Internal stress concentration | FSI | Tensile testing Strain sensors | Minimize |
| | Stress-strain behavior | FSI | Tensile testing | Physiologic range |
| Long-term Performance | Durability | — | Accelerated testing | Maximize |
| | Thrombogenicity | — | Opacity Mass Biochemistry | Minimize |

CFD = Computational Fluid Dynamics;
FSI = Fluid Structure Interaction;
PIV = Particle Image Velocimetry In some implementations, the CFD engine 126 can model the cardiovascular physiology using fluid-structure interactions to quantify the deformation and stresses on vessel walls. Adoption of fluid-structure interactions with spatially varying properties better captured the wave propagation phenomena, which yielded a greater match to in vivo dynamic imaging.

Example 3

Due to the large number of parameters and the complex nature of design objectives involved, prior CFD designs of CABGs often employed overly simplistic assumptions—including idealized anatomy, rigid walls and unrealistic boundary conditions—and have approached solutions through "trial-and-error." In some implementations, the controller 104 can unite computer-aided design, CFD, fluid-structure interactions, and optimization methods to provide a fuller exploration of the permutations and combinations of physiologically important variables. As an example, the anastomotic angle between the CABG and the coronary artery can affect hemodynamics considerably. FIG. 4 illustrates marked differences in velocity and WSS to different angles of distal graft anastomosis in same coronary segment. These computational evaluations can be employed to reduce energy loss and endothelial damage caused by flow impingements at the native artery, while keeping WSS in the physiologic range and abnormal recirculating flow restricted to a minimal area. The controller 104 can use a derivative-free approach to search the large design space to identify optimal CABG designs that satisfy the requirement of minimizing unfavorable flow conditions across a range of physiologic conditions (e.g., rest and exercise); and allows for thorough yet parsimonious selection of integrated designs that can be implemented and tested in vitro.

Example 4

The in vitro measurements were performed in a benchtop flow circulation systems using patient-specific SDVG physical models fabricated by the printing subsystem 102 (e.g., a multi-material high-resolution 3D printing system). The experiments demonstrated that the system 100 can produce complex 3D arterial geometries with continuously spatially varying mechanical properties. FIG. 5A illustrates the patient-specific SDVG 122 as a 3D printed physical model. The 3D printed physical model can be evaluated for patient-specific, graft-specific and surgical technique-related factors that affect SDVG hemodynamics and wall mechanics by 3 distinct methods: (i) intravascular pressure and flow sensors, (ii) particle image velocimetry (PIV) and (iii) embedded soft strain sensors.

Figure 6:
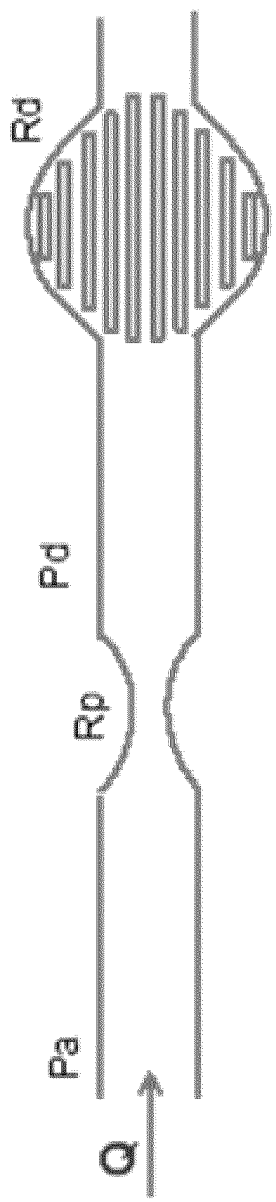
FIG. 6 illustrates an in vitro benchtop flow system generating realistic pressure using downstream resistance based upon physiologically prescribed flow.

FIGS. 5B and 6 illustrate an in vitro flow circulation system that was constructed that approximates coronary flow physiology to determine the relationship between an input defined flow rate (Q), proximal (Pa) and distal (Pd) pressures, and the resistance of a stenosis (Rp) and distal microvasculature (Rd). The flow circulation system can include a programmable flow pump, patient-specific vascular models, downstream resistance modules, and intravascular pressure and flow sensors. In the flow circulation system, a coronary artery was made with a 50% stenosis using 3D printing, and used the pump to prescribe three flow rates, with varying microvascular resistance to match four levels of proximal pressures. Distal pressure differed markedly according to perturbations in flow and resistance, and confirmed the importance of inflow/outflow conditions to optimize within-vessel pressures.

PIV was also integrated into the flow circulation system. FIGS. 5C and 5D illustrate the tracking of particle movements and computing of pulsatile fluid velocities within small-diameter tubular models. Velocity measurements by PIV were in accordance with pressure measurements described above, and demonstrate that the integration of in vitro flow and PIV systems allows us to not only measure pressure, but also velocities with high spatial (about 20 µm) and temporal resolution (about 100 Hz).

In some implementations, 3D printed soft strain sensors, generated by direct nozzle extrusion of conductive hydrogels and dielectric elastomers, are incorporated into the SDVG. The sensor's softness (<1 MPa) and small size (<0.5 mm total thickness) allow integration within SDVG for continuous monitoring of strain profiles. This technique is advantageous because multiple sensors can be embedded at different positions within the SDVG. A sampling of hemodynamics and mechanics that can be evaluated by the sensors is listed in Table 2.

Example 5

Figure 7:
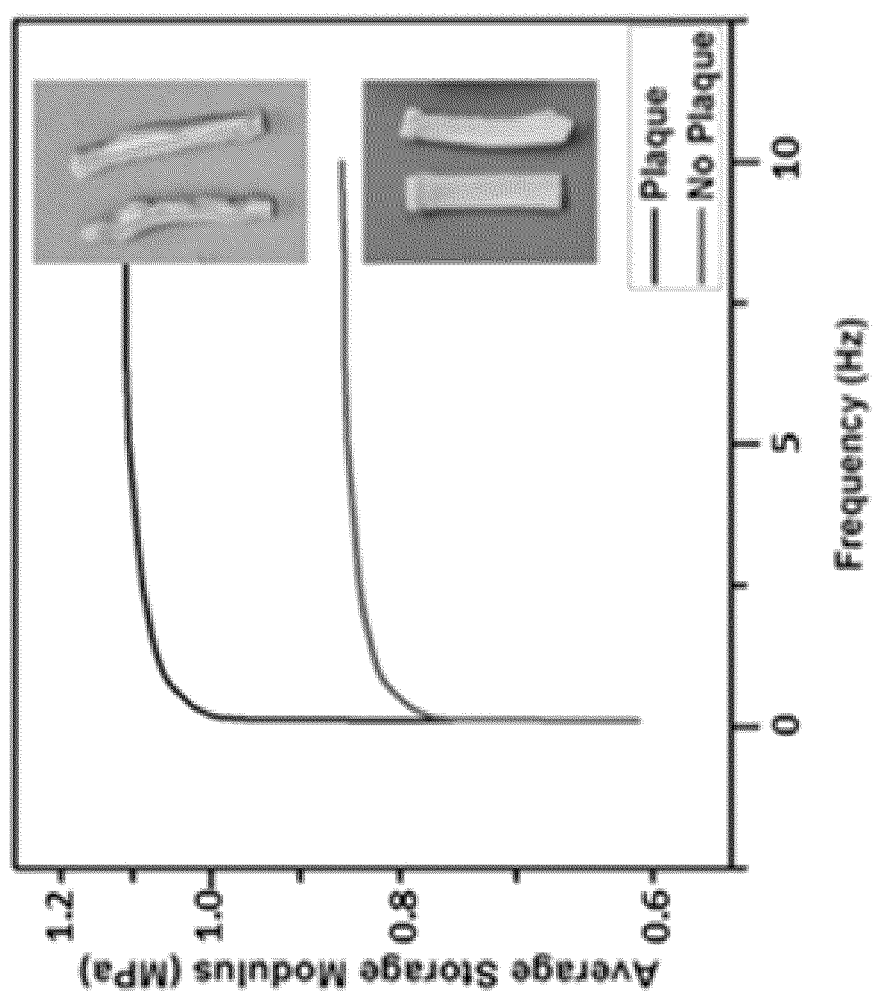
FIG. 7 illustrates example mechanical properties of fixed aorta tissue.

FIG. 7 illustrates the mechanical properties of a coronary artery. In some implementations, the system 100 can generate the patient-specific SDVG 122 responsive to the mechanical properties of the coronary artery such that the patient-specific SDVG 122 has biomimetic features that offer the favorable hemodynamics, biocompatibility, and durability.

Example 6

Figure 8:
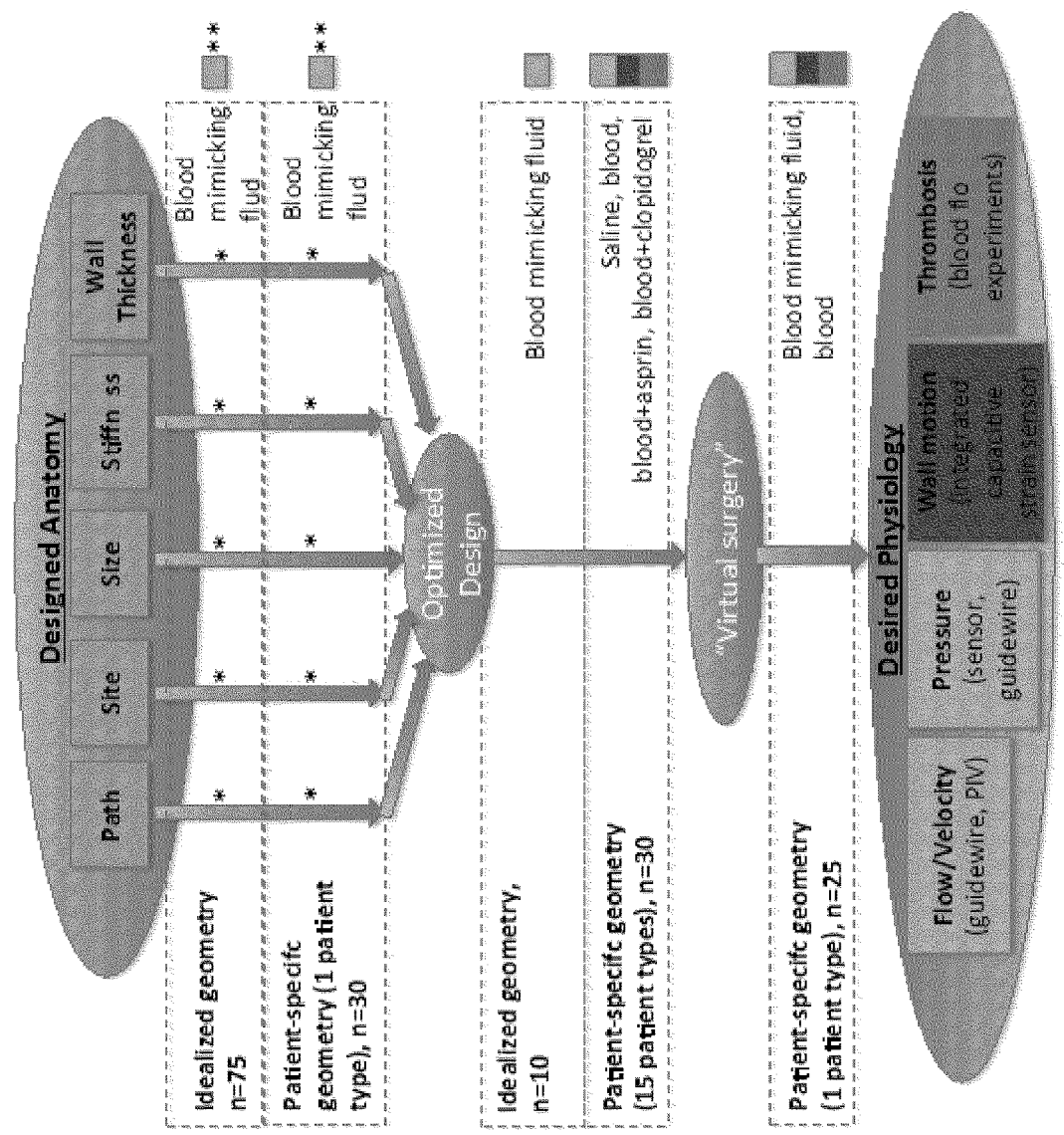
FIG. 8 illustrates an example flow diagram of an experiment.

FIG. 8 illustrates a tiered approach to validate a SDVG for CABG surgery using in silico, in vitro, and in vivo methods. The optimized SDVG will be tested in a flow system with patient-specific anatomy fabricated by 3D printing (in vitro) as described herein. Both the in silico and the in vitro work will yield an optimized patient-specific CABG, whose performance will be validated in vivo in swine.

Example 7

In some implementations, the anatomical engine 124 can perform cardiac segmentation in a mathematical model-based method by employing machine learning to automatically delineate structures in the thorax by capitalizing on the relative stability of the spatial and topological relationship between different organs. A medial model, which equally divides the organ wall into inner and outer layers by implicit thickness definition, can be used as the cardiothoracic shape template. The segmentation can be used to detected landmarks for the establishment of an affine transform, which allows deforming the template to the image volume to be segmented. The template surface of each structure is then refined so that the template surfaces correctly align with the target boundaries in the image.

Example 8

In some implementations, given the proximal and distal anastomosis sites $A_p$ and $A_d$, the geometry of patient-specific SDVG can be parameterized by coordinates of the control nodes in between $c_1, \ldots, c_I$ and diameters, $d_1, \ldots d_J$. Therefore, the smooth patient-specific SDVG model can be uniquely defined by a combination of these primary parameters. Other common variables such as orifice size at the anastomosis, graft length, and curvature are derived from the primary parameters (Table 3). Design of the patient-specific SDVG surface model can include defining a local coordinate frame [t,u,v] at each node using a rotation minimization technique, where t is along the tangent direction of the centerline and [u,v] spans a 2D plane on the cross-section. The graft surface is created as a structured mesh by sweeping through the contours on the 2D planes, which is extremely fast and allows for both real-time interactive editing and programmable modified by an algorithm.

In some implementations, the anatomical engine 124 can employ a collision detection method. The collision detection method can avoid the path of the graft passing through the segmented critical anatomic structures (e.g., pulmonary artery) by constraining the search space of the parameters. Collision is detected via a two-step accelerated algorithm by checking whether the graft crosses the bounding box of the critical structures, and then verifying that the graft passes through the critical structures themselves. The speed of the second step may be improved by inserting the surface triangles into a tree data structure, e.g., the AABB tree, which decreases the computational complexity from O(n) to O(lgn). To prevent the complex twisted, elongated and tortuous pathways commonly seen in vein grafts, the anatomical engine 124 can use a method to search for the path of minimal length and curvature, satisfying the following conditions: both ends correspond to proximal and distal anastomosis sites and the path of the graft does not cross critical structures. Search based dynamic programming can be used by alternating between proposing a simplified path candidate and varying the path to avoid collision.

TABLE 3

| CABG Design Parameters | Design Constraint and Consideration |
| --- | --- |
| Graft path | Critical cardiothoracic structures |
|  | Graft length and curvature |
| Graft diameter | Coronary artery diameter |
|  | Anastomosis orifice size |
| Anastomosis sites | Aortic and coronary anatomy |
|  | Location of coronary stenosis |
| Anastomosis geometry | Coronary artery diameter |
|  | Anastomosis angle |
|  | Ease of Anastomosis |
| Wall mechanical properties | Aorta and coronary artery stiffness |
|  | Cardiac motion |
| Wall thickness | Graft strength |
|  | Graft weight |

Example 9

In some implementations the CFD engine 126 can generate boundary conditions for the graft wall. For the fluid-structure interactions method, fluid structure interaction based on the Arbitrary Lagrangian-Eulerian Method can be used. The methods can couple the wall mechanics and the blood flow together and can be capable of handling potential large displacements. In some implementations, external structures attached to the vessels and the graft can be modeled using lumped boundary conditions. To test the efficiency of flow augmentation by the graft and to avoid high power assumption and damage risk, the stiffness and strength of the materials can be another set of parameters used to calculate the wall thickness t and the mechanical stiffness E of the patient-specific SDVG (Table 3). Allowing spatial variation of these parameters provide extra flexibility that the graft should match at both anastomoses to the differing stiffness of the aorta and coronary arteries.

Example 10

In some implementations, the CFD engine 126 can determine the influence of the local hemodynamics in the patient-specific SDVG and how the patient-specific SDVG changes the downstream blood flow patterns. The CFD engine 126 can improve the patient-specific SDVG design using CFD, objective functions, and hemodynamic variables (Table 2) of interest, e.g., flow rate, pressure gradient, shear stress and traction on the wall, flow oscillation and separation, energy loss, graft motion and deformation, or a combination of several variables.

In some implementations, the hemodynamic objective functions can be combined with shape-based features, such as curvature or length to avoid overly complex geometry. A general patient-specific SDVG optimization problem can be written as min F(P), s.t. $G_{min} \leq G(P) \leq G_{max}$, where P is a vector of all parameters in patient-specific SDVG design, and F(P) is the target function to be optimized, e.g., maximizing the flow rate in the patient-specific SDVG. G(P) represents the list of constraints in the hemodynamic targets that fall between the preferred ranges $G_{min}$ and $G_{max}$. First, the most sensitive parameters will be chosen to optimize for the variable of interest. For example, wall stiffness may be omitted when WSS is considered; WSS varies only 5% with different levels of stiffness in physiologic ranges.

Example 11

In some implementations, the 124 can use both idealized and patient-specific geometries from a group of patients to generate the patient-specific SDVG. The idealized geometry will include cylindrical shapes of ascending aorta and several coronary arteries, which is useful to generate plausible data before adding geometric complexity, especially when simulating for novel strategies. For patient-specific evaluation, common geometries and potential failure modes will be identified. To address the possibility that an overall optimal design may be achieved by a combination of parameters when each parameter is suboptimal, an iterative approach by repeating the optimization under the updated parameters will be used. Qualitative and quantitative analysis will be performed to determine conceptual soundness, generalizability and statistical significance of such findings.

Example 12

In some implementations, the CFD engine 126 calculates hemodynamics and wall mechanics variables using: (i) pressure measurements received from pressure gauges, (ii) pressure and flow measurements received from guidewires, (iii) flow velocities received response to PIV, particle residence time, and oscillation, and (iv) strain measurements.

Example 13

In some implementations, the system can evaluate the effects of any given variable on hemodynamics by fixing the geometry of the aorta and coronary arteries. This is done to identify an optimal patient-specific SDVG geometry without the need to initially consider wall deformation. Single geometric variables that have been suggested by the CFD engine 126 and fluid-structure interactions are explored one-by-one, and systematically varied to determine their weighted effects.

Single variables that can improve hemodynamics are assessed in combination with each other to determine their additive or synergistic improvement effects, as well as fluid-structure interactions-predicted contributions by using elastic walls. Patient-specific SDVGs can be produced in a step-wise fashion to determine the salutary effects of any individual variable on a multivariable integrated SDVG.

Upon identifying the optimal SDVG design over this wide parameter space, patient-specific models based upon CTA are evaluated by the CFD engine 126. Cardiothoracic anatomy and native coronary artery mechanical property information are included in the evaluation. The models are tested on different patient types. Patients that differ in the following anatomic findings are chosen: (i) cardiothoracic size and geometry; (ii) aortic size, tortuosity and location, (iii) coronary artery size, tortuosity and location, and (iv) coronary artery disease extent and severity.

Example 14

The benefits of the optimized SDVG may be mitigated when implanted in vivo due to the complexity and variability in surgical techniques. To account for this, "benchtop surgery" in vitro to assess the sensitivity needed to realize beneficial SDVG hemodynamics is performed. For example, if significant variability is present from SDVG angles, orientation markers to the surgeon for ideal SDVG angle deployment are provided. Likewise, SDVGs with orifices that cannot be sutured to less than a certain size can be produced. In some embodiments, "benchtop surgery" physical models included within-subject controls using polyurethane and, if additive, polytetrafluoroethylene (PTFE), expanded polytetrafluoroethylene (ePTFE), and polyethylene terephthalate (PET).

Example 15

To ensure the optimized SDVG has sufficient durability to withstand the long-term cyclical strains in vivo, accelerated cyclic durability tests will be performed. These tests will include of applying strains, slightly higher than physiological levels (~40% radial strain) at a frequency 5 times higher than that of the normal heart rate. Testing will be conducted for 18 days, and will therefore assess the durability of the optimized SDVG equivalent to normal conditions for 90 days.

Example 16

Reductions in thrombogenicity may occur through optimizing SDVG hemodynamics and wall mechanics. The thromboresistive nature of fabricated SDVGs will be assayed by the following methods: (i) optical methods that identify changes in opacity in transparent SDVGs to characterize time, size and distribution of thrombi formation; (ii) mass measurements using change in weight of SDVG before and after blood perfusion; and (iii) platelet activity using low shear impedance aggregometry and hematologic parameters. Non-treated blood, blood treated with aspirin (81 mg equivalent), and aspirin plus clopidogrel (75 mg equivalent) will be tested. Aspirin and aspirin plus clopidogrel treatments will be considered standard-of-care for individuals post-CABG. Optimized CABGs will be compared to other SDVG, including polyurethane, ePTFE, and polyethylene terephthalate. OCT will be used to evaluate both durability and thrombogenicity. For durability, surface details of the SDVG will be examined and thrombosis will be monitored after whole blood circulation for fabricated SDVGs that are not transparent.

Example 17

The efficacy and safety of optimized SDVGs in vivo in naïve domestic swine will be assayed, with a primary endpoint of the 90-day patency rates of optimized CABG SDVGs compared to conventional polyurethane SDVG controls. Patency will be assessed by gross inspection, intravascular imaging and pathology. Other factors that will be monitored include: (i) safety, (ii) assessment of native coronary vessels for thrombosis or occlusion, and (iii) assessment of device performance and handling. Safety will be evaluated through gross and histological analysis of (a) morphometry parameters (internal elastic membrane (IEM)-based % stenosis, neointimal thickness and area, medial area and lumen area, IEL and external elastic membrane area); (b) morphology parameters (including scoring for inflammation, thrombus, endothelialization, medial smooth muscle cell proliferation or loss, fibrin deposition, injury and fibrosis); (c) scanning electron microscopy of a subset of vessels for endothelialization and micro-thrombus formation; and (d) documentation of device-related adverse events.

Figure 9:
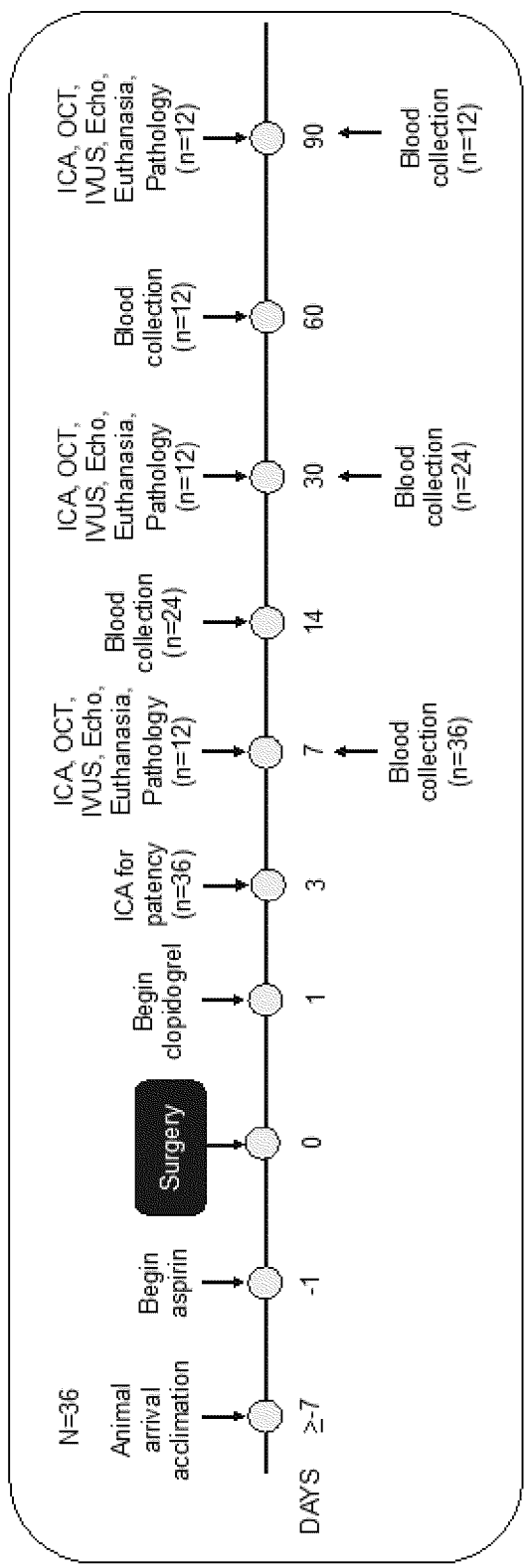
FIG. 9 illustrates an example experimental timeline.

FIG. 9 illustrates the timeline for swine undergoing coronary artery bypass surgery. Surgery will be performed at the CRF Skirball Center for Intervention. All grafts will be anastomosed in end-to-side fashion. All subjects will receive aspirin preoperatively, with clopidogrel initiated the day after surgery, in accordance with treatment for patients undergoing CABG. Days-to-euthanasia will be 7, 30 and 90, with echocardiography, intravascular imaging (by angiography, OCT and intravascular ultrasound [IVUS]) performed before termination. Non-terminal echocardiography at 7, 30, and 90 days for animals that have not been euthanized will be performed.

Figure 10:
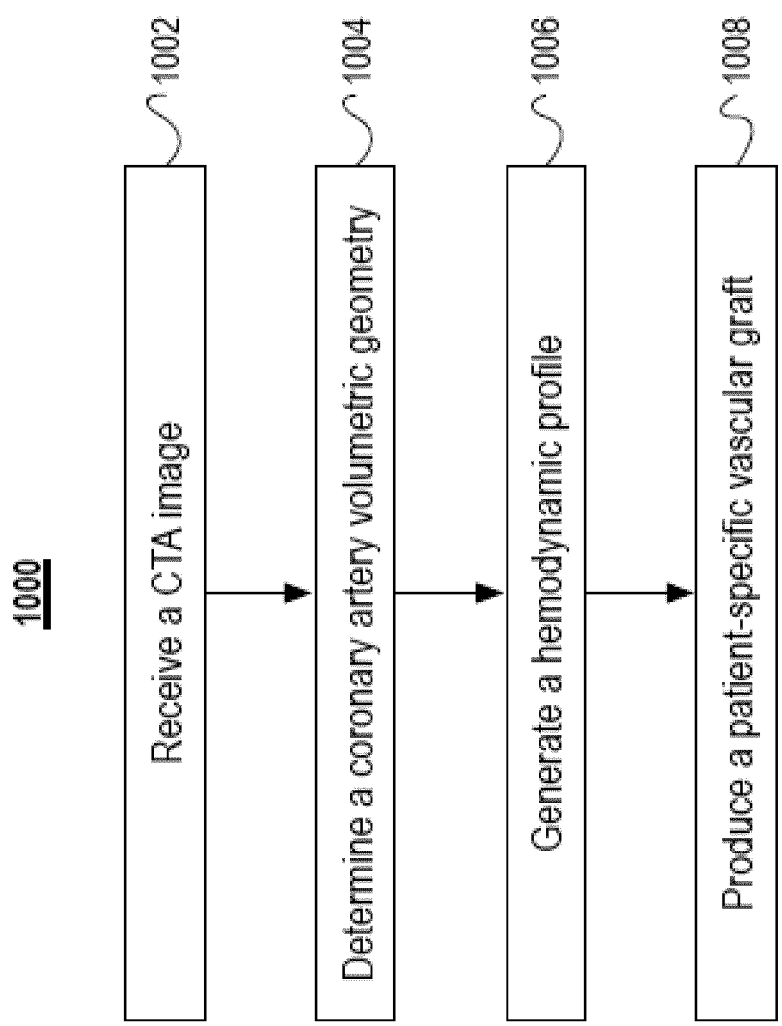
FIG. 10 illustrates an example method for producing a patient-specific vascular graft using the system illustrated in FIG. 1.

Thirty-six naïve domestic swine will undergo surgery with appropriate within-subject and between-subject controls (FIG. 10). CABG surgical models account for the number of bypassed vessels (⅓ vs. 3/3), the % stenosis in the native coronary vessels (70% vs. 100%) and the specific vessels being bypassed (left anterior descending, left circumflex or right coronary arteries) with a conventional polyurethane graft as a comparator in each case (Table 4). To maximize the number of optimized CABGs for evaluation, surgeries will be performed in a 2:1 ratio (e.g., optimized CABG:polyurethane control) for all between-subject comparisons.

Swine will be analyzed by (a) laboratory analysis, (b) echocardiography, (c) intravascular imaging (ICA, OCT and IVUS), and (d) pathology. Intravascular imaging and pathology will be performed only at the terminal date prior to euthanasia. Blinded expert core laboratory readers will perform all imaging (Cardiovascular Research Foundation or Dalio Institute of Cardiovascular Imaging, New York, N.Y.) and pathology studies (CV Path, Gaithersburg, Md.).

Laboratory Analysis.

Blood samples will be evaluated following overnight fast for hematology, chemistry, and fibrinogen.

Echocardiography.

Transthoracic echocardiography will be performed emphasizing surrogate markers of graft closure (e.g., ejection fraction, ventricular wall motion abnormalities, and diastolic function).

Intravascular Imaging.

Intravascular imaging will be performed at termination. ICA will be performed in accordance with societal guidelines to assess SDVG patency. ICAs will be evaluated by quantitative coronary angiographic (QCA) for stenosis severity. OCT—with its high spatial (10 µm) resolution—will be used to evaluate two complications of the optimized CABG: thrombogenicity and structural defects, but can also assess atheroma, macrophage accumulation, and intimal hyperplasia. IVUS will be used for tissue characterization of stenosis and intimal hyperplasia; as well as for external and internal elastic lamina area, lumen area; and derived values of neointimal area and thickness, medial area, and lumen diameter.

Pathology will be performed post-mortem. Vessels will be perfusion fixed, with test arteries and SDVGs excised as a whole. Treated vessels will be examined by a pathologist for vessel laceration, hematoma, or thrombus associated with the treatment and/or delivery system. All samples will be embedded in paraffin, sectioned and stained, then subjected to analysis for biological responses, including inflammation, thrombus, endothelialization, intimal hyperplasia, fibrin deposition, injury, hemorrhage, and necrosis.

FIG. 10 illustrates an example method 1000 for producing a patient-specific vascular graft. The method 1000 includes receiving at least one CTA image of a subject (step 1002). The method 1000 includes determining a coronary artery volumetric geometry responsive to the CTA image (step 1004). The method 1000 also includes generating a hemodynamic profile (step 1006). The method 1000 also includes producing a patient-specific vascular graft (step 1008).

TABLE 4

| Comparator | # Bypassed Vessels | % Stenosis Native Vessel(s) | LAD | LCx | RCA | N (=36) |
| --- | --- | --- | --- | --- | --- | --- |
| Between-subject | 1 | 70% | oCABG | None | None | 6 |
| Between-subject | 1 | 70% | PU | None | None | 3 |
| Between-subject | 1 | 100% | OCABG | None | None | 6 |
| Between-subject | 1 | 100% | PU | None | None | 3 |
| Within-subject | 3 | 70% | oCABG | oCABG | PU | 3 |
| Within-subject | 3 | 70% | oCABG | PU | oCABG | 3 |
| Within-subject | 3 | 70% | PU | oCABG | oCABG | 3 |
| Within-subject | 3 | 100% | oCABG | oCABG | PU | 3 |
| Within-subject | 3 | 100% | oCABG | PU | oCABG | 3 |
| Within-subject | 3 | 100% | PU | oCABG | oCABG | 3 |

LAD = Left anterior descending artery;
LCx = Left circumflex artery;
RCA = Right coronary artery;
oCABG = optimized CABG;
Pu = polyurethane As set forth above, the method 1000 includes receiving CTA image data (step 1002). In some implementations, the CTA image data includes image data of a patient's heart or vascular system. The image data can include image data of small diameter arteries and veins. In some implementations, the patient is given an iodine-rich contrast material prior to imaging by a computer tomography device. It should be understood that, in some implementations, the method 1000 can instead be carried out using a different type of medical image. For example, instead of receiving a CTA image, the method 1000 can include receiving an MRI or MRA image.

The method 1000 can also include determining a coronary artery volumetric geometry (step 1004). In some implementations, determining the coronary artery volumetric geometry can include determining an artery centerline of the patient's coronary artery (or other artery). The method 1000 can also include segmenting the coronary artery volumetric geometry.

The method 1000 can also include generating a hemodynamic profile (step 1006). In some implementations, the hemodynamic profile can include clinical factors (e.g., any of the factors shown in Table 2) and design factors (e.g., any of the factors shown in Table 3), which may include flow oscillation, flow stagnation, flow energy loss, wall mechanics, shear levels, and graft-artery compliance mismatch.

The method 1000 can also include producing the patient-specific vascular graft (step 1008). As described above, the graft can be produced with a 3D printer. In some implementations, the graft can have an internal diameter between about 0.5 mm and about 6 mm. In some implementations, the 3D printer is a multi-material bioprinting stereolithography system that can fabricate complex composite cellular seeded hydrogels. In some implementations, the 3D printer can print the patient-specific vascular graft using at least one biocompatible polymer. For example, biocompatible polymers may include urethanes, silicone, PET, PTFE, and ePTFE. The 3D printer also can be configured to print the patient-specific vascular graft such that the patient-specific vascular graft exhibits continuously spatially varying mechanical properties along at least a portion of its length. In some implementations, this can be achieved by varying the materials (or combinations of materials) used to form the patient-specific vascular graft or by varying a wall thickness of the patient specific vascular graft along the length of the graft.

In some implementations, determining the coronary artery volumetric geometry (step 1004) can include determining an artery centerline of the coronary artery. The method 1000 also can include forming lumen segmentation of the coronary artery volumetric geometry, as discussed above.

In some implementations, the method 1000 also includes calculating at least one of a flow, a velocity, a pressure, or a shear stress of the patient-specific vascular graft. For example, the patient-specific vascular graft can be incorporated into a flow system having a pump and at least one measurement tool, such as a pressure gauge, a flow gauge, a velocity gauge, a particle image velocimetry device, a pressure guide wire, a flow guide wire, an optical coherence tomography device, or a strain sensor. In some implementations, measuring the flow characteristics and performances in the 3D printed patient-specific vascular graft can better approximate the flow characteristics and performances of the patient's anatomy when compared to computational models of the flow characteristics and performances. An example of such a flow system is described below in connection with FIG. 11. In some implementations, generating the hemodynamic profile (step 1006) can be achieved by applying an optimization technique based on a set of parameters including at least one of a flow rate, a pressure gradient, a shear stress, or a flow oscillation. The choice may closely depend on the design target (e.g. maximizing flow or increasing shear stress) and may sometimes lead to compromise. For example, increasing the graft diameter may augment the flow rate, but shear stress may be decreased to abnormal ranges as a result. In addition, experimental studies have shown certain variables are considered normal when falling in a safe range. Further, hemodynamic objective functions can be combined with shape-based features of the patient-specific vascular graft, such as curvature or length, to avoid overly complex geometry. A general optimization problem can be written as min F(P), s.t. $G_{min} \leq G(P) \leq G_{max}$, where P is a vector of all parameters in graft design, and F(P) is the target function to be optimized, e.g. maximizing the flow rate in the graft. G(P) represents the list of constraints in the hemodynamic targets that fall between the preferred ranges $G_{min}$ and $G_{max}$. While the optimization is difficult to solve because of unavailable gradient and expensive functional evaluation of F(P) and G(P), the problem may be simplified by limiting the number of variables and parameters involved, automating the procedures of shape design and execution, and taking advantage of derivative-free algorithms. In some implementations, the most sensitive parameters can be chosen to optimize for the variable of interest. For instance, wall stiffness may be omitted when WSS is considered WSS varies only 5% with different levels of stiffness in physiologic ranges. In some implementations, a derivative-free method, e.g. Nelder-Mead method or genetic algorithms may be used to perform optimization tasks.

Figure 11:
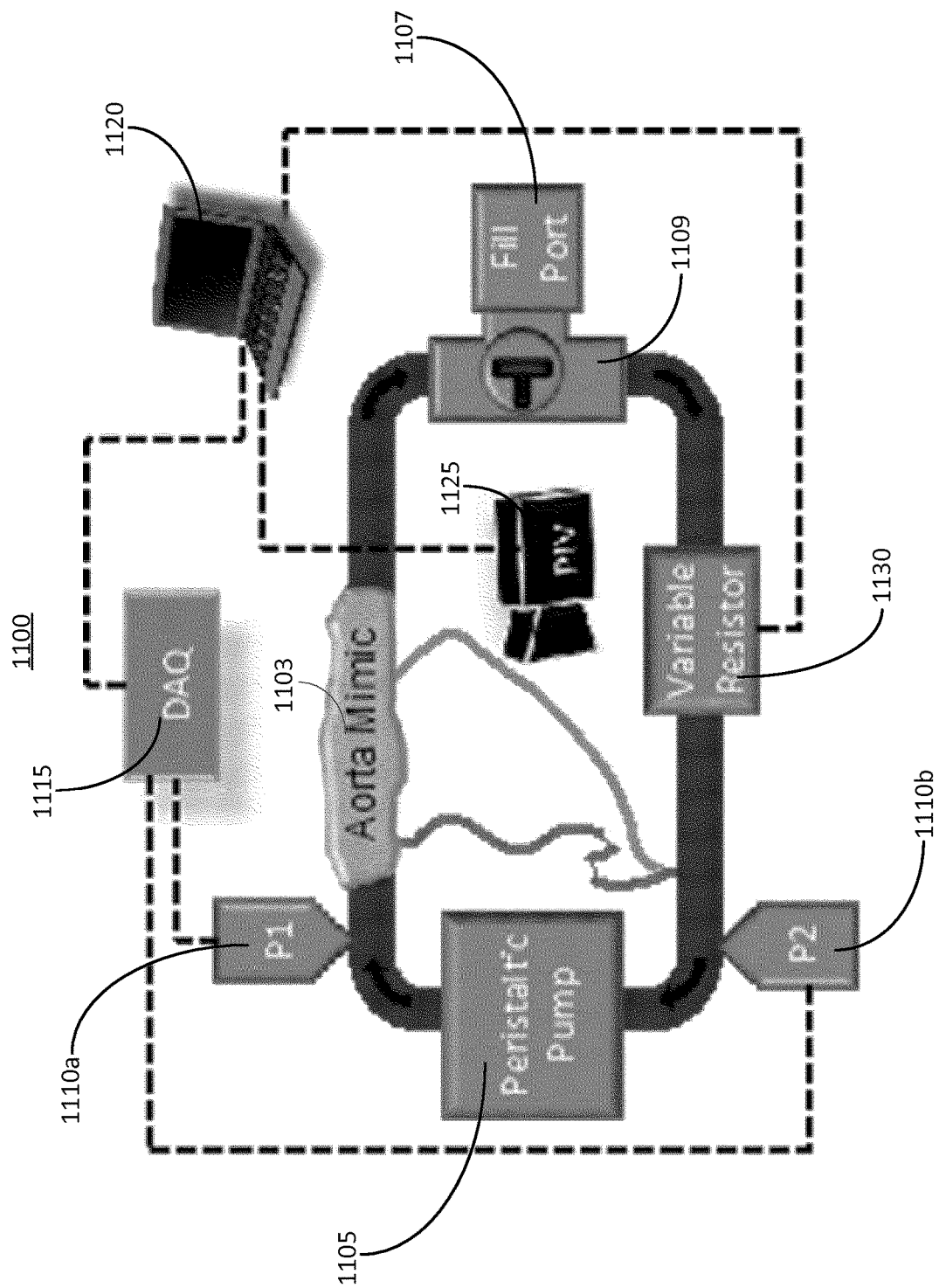
FIG. 11 illustrates an example flow system with a patient-specific vascular graft.

FIG. 11 illustrates an example flow system 1100 with a patient-specific vascular graft. The system 1100 includes the patient-specific vascular graft 1103 (labeled in FIG. 11 as an aorta mimic), a stenosed coronary artery 1107 coupled to a fill port 1109. The patient-specific components of the system 1100 can be generated with the 3D printing methods described herein. The system 1100 also includes a peristaltic pump 1105, pressure sensors 1110a and 1110b (generally referred to as pressure sensors 1110), a data-acquisition board (DAQ) 1115, a computing device 1120, and PIV device 1125. The system 1100 can mimic idealized or patient-specific physical models of the aorta, coronary arteries and optimized CABG, including single or diffuse stenosis, and coronary collateral circulations that contribute to competing flow. Coronary-specific in vitro boundary conditions can be developed to generate realistic coronary pressure waveforms by combining resistors and capacitors, such as the variable resistor 1130. Further, calibration of the system 1100 can be performed against a unique multicenter database, which may include more than 250 patient-specific CTAs and location-specific invasive gold standard pressure measurements. The system 1100 can accommodate a variety of measurement tools, including pressure, flow and velocity gauges (such as the pressure sensors 1110); the PIV device 1125; pressure and flow guide-wires; an optical coherence tomography (OCT) device; and integrated strain sensors. The computing device 1120 can receive information from any of these measurement tools, and can process the information to evaluate the physical model represented by the system 1100. Thus, the system 1100 can enable "benchtop surgery," allowing optimized CABGs to be physically sutured to the physical models.

An embodiment of the disclosure relates to a non-transitory computer-readable storage medium having computer code thereon for performing various computer-implemented operations. The term "computer-readable storage medium" is used herein to include any medium that is capable of storing or encoding a sequence of instructions or computer codes for performing the operations, methodologies, and techniques described herein. The media and computer code may be those specially designed and constructed for the purposes of the embodiments of the disclosure, or they may be of the kind well known and available to those having skill in the computer software arts. Examples of computer-readable storage media include, but are not limited to: magnetic media such as hard disks, floppy disks, and magnetic tape; optical media such as CD-ROMs and holographic devices; magneto-optical media such as optical disks; and hardware devices that are specially configured to store and execute program code, such as application-specific integrated circuits (ASICs), programmable logic devices (PLDs), and ROM and RAM devices.

Examples of computer code include machine code, such as produced by a compiler, and files containing higher-level code that are executed by a computer using an interpreter or a compiler. For example, an embodiment of the disclosure may be implemented using Java, C++, or other object-oriented programming language and development tools. Additional examples of computer code include encrypted code and compressed code. Moreover, an embodiment of the disclosure may be downloaded as a computer program product, which may be transferred from a remote computer (e.g., a server computer) to a requesting computer (e.g., a client computer or a different server computer) via a transmission channel. Another embodiment of the disclosure may be implemented in hardwired circuitry in place of, or in combination with, machine-executable software instructions.

As used herein, the singular terms "a," "an," and "the" may include plural referents unless the context clearly dictates otherwise.

As used herein, relative terms, such as "above," "below," "up," "left," "right," "down," "top," "bottom," "vertical," "horizontal," "side," "higher," "lower," "upper," "over," "under," "inner," "interior," "outer," "exterior," "front," "back," "upwardly," "lower," "downwardly," "vertical," "vertically," "lateral," "laterally" and the like refer to an orientation of a set of components with respect to one another; this orientation is in accordance with the drawings, but is not required during manufacturing or use.

As used herein, the terms "connect," "connected," and "connection" refer to an operational coupling or linking. Connected components can be directly or indirectly coupled to one another, for example, through another set of components.

As used herein, the terms "approximately," "substantially," "substantial" and "about" are used to describe and account for small variations. When used in conjunction with an event or circumstance, the terms can refer to instances in which the event or circumstance occurs precisely as well as instances in which the event or circumstance occurs to a close approximation. For example, when used in conjunction with a numerical value, the terms can refer to a range of variation less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. For example, two numerical values can be deemed to be "substantially" the same if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified.

While the present disclosure has been described and illustrated with reference to specific embodiments thereof, these descriptions and illustrations do not limit the present disclosure. It should be understood by those skilled in the art that various changes may be made and equivalents may be substituted without departing from the true spirit and scope of the present disclosure as defined by the appended claims. The illustrations may not be necessarily drawn to scale. There may be distinctions between the artistic renditions in the present disclosure and the actual apparatus due to manufacturing processes and tolerances. There may be other embodiments of the present disclosure which are not specifically illustrated. The specification and drawings are to be regarded as illustrative rather than restrictive. Modifications may be made to adapt a particular situation, material, composition of matter, technique, or process to the objective, spirit and scope of the present disclosure. All such modifications are intended to be within the scope of the claims appended hereto. While the techniques disclosed herein have been described with reference to particular operations performed in a particular order, it will be understood that these operations may be combined, sub-divided, or re-ordered to form an equivalent technique without departing from the teachings of the present disclosure. Accordingly, unless specifically indicated herein, the order and grouping of the operations are not limitations of the present disclosure.

What is claimed is:

1. A method comprising:
   receiving at least one medical image of a subject;
   determining a coronary artery volumetric geometry of the subject responsive to the at least one medical image;
   determining, using the coronary artery volumetric geometry of the subject, a subject-specific hemodynamic profile that quantifies, based on subject-specific fluid-structure interactions, deformation and stress on vessel walls of the subject;
   generating a subject-specific vascular graft model using the coronary artery volumetric geometry and the subject-specific hemodynamic profile, wherein generating the subject-specific vascular graft model includes defining one or more subject-specific design parameters based on the deformation and stress on the vessel walls of the subject; and
   producing a subject-specific vascular graft according to the subject-specific vascular graft model.

2. The method of claim 1, wherein producing the subject-specific vascular graft includes three-dimensional (3D) printing the subject-specific vascular graft model using a 3D printer.

3. The method of claim 2, wherein the subject-specific vascular graft is formed from a biocompatible polymer.

4. The method of claim 2, wherein the subject-specific vascular graft exhibits continuously spatially varying mechanical properties along at least a portion of its length.

5. The method of claim 1, wherein the subject-specific vascular graft has an internal diameter between about 0.5 mm and about 6 mm.

6. The method of claim 1, wherein determining the coronary artery volumetric geometry comprises determining an artery centerline of the coronary artery.

7. The method of claim 1, further comprising performing lumen segmentation of the coronary artery volumetric geometry.

8. The method of claim 1, wherein determining the hemodynamic profile includes applying computational fluid dynamics (CFD) to calculate at least one of a flow, a velocity, a pressure, or a shear stress.

9. The method of claim 8, further comprising calculating at least one of the flow, the velocity, the pressure, or the shear stress of the subject-specific vascular graft using a flow system comprising a pump, the subject-specific vascular graft, and at least one measurement tool.

10. The method of claim 9, wherein the at least one measurement tool comprises at least one of a pressure gauge, a flow gauge, a velocity gauge, a particle image velocimetry device, a pressure guide wire, a flow guide wire, an optical coherence tomography device, or a strain sensor.

11. The method of claim 1, wherein determining the subject-specific hemodynamic profile further comprises applying an optimization technique based on a set of parameters including at least one of a flow rate, a pressure gradient, a shear stress, or a flow oscillation.

12. The method of claim 1, wherein the at least one medical image comprises at least one computed tomographic angiography image.

13. A system comprising at least one processor and a memory unit storing processor executable instructions, wherein execution of the processor executable instructions by the at least one processor causes the at least one processor to:
receive at least one medical image of a subject;
determine a coronary artery volumetric geometry of the subject responsive to the at least one medical image;
determine, using the coronary artery volumetric geometry of the subject, a subject-specific hemodynamic profile that quantifies, based on subject-specific fluid-structure interactions, deformation and stress on vessel walls of the subject;
generate a subject-specific vascular graph model using the coronary artery volumetric geometry and the subject-specific hemodynamic profile, wherein generating the subject-specific vascular graft model includes defining one or more subject-specific design parameters based on the deformation and stress on the vessel walls of the subject; and
generate instructions for producing a subject-specific vascular graft according to the subject-specific vascular graft model.

14. The system of claim 13, wherein execution of the processor executable instructions further causes the at least one processor to generate instructions for three-dimensional (3D) printing the subject-specific vascular graph model by a 3D printer.

15. The system of claim 14, wherein the instructions for producing the subject-specific vascular graft indicate that the subject-specific vascular graft is formed from a biocompatible polymer.

16. The system of claim 14, wherein the instructions for producing the subject-specific vascular graft indicate that the subject-specific vascular graft has continuously spatially varying mechanical properties along at least a portion of its length.

17. The system of claim 13, wherein execution of the processor executable instructions further causes the at least one processor to determine the coronary artery volumetric geometry by determining an artery centerline of the subject.

18. The system of claim 13, wherein execution of the processor executable instructions further causes the at least one processor to perform a lumen segmentation of the coronary artery volumetric geometry.

19. The system of claim 13, wherein execution of the processor executable instructions further causes the at least one processor to apply computational fluid dynamics (CFD) to calculate at least one of a flow, a velocity, a pressure, or a shear stress of the patient-specific vascular graft model.

20. The system of claim 19, wherein execution of the processor executable instructions further causes the processor to calculate at least one of the flow, the velocity, the pressure, or the shear stress of the subject-specific vascular graft model based on an output received from at least one measurement tool included within a flow system that also comprises a pump and the subject-specific vascular graft.

21. The system of claim 20, wherein the at least one measurement tool comprises at least one of a pressure gauge, a flow gauge, a velocity gauge, a particle image velocimetry device, a pressure guide wire, a flow guide wire, an optical coherence tomography device, or a strain sensor.

22. The system of claim 13, wherein the at least one medical image comprises at least one computed tomographic angiography image.

* * * * *